(12) United States Patent
Shah et al.

(10) Patent No.: US 11,737,684 B2
(45) Date of Patent: Aug. 29, 2023

(54) ENERGY EXPENSE DETERMINATION FROM SPATIOTEMPORAL DATA

(71) Applicant: Yur Inc., San Mateo, CA (US)

(72) Inventors: Dilan Shah, San Francisco, CA (US); Ethan McCosby, New Castle, PA (US); Cix Liv, San Francisco, CA (US); Maximilian Meyers, Henrico, VA (US)

(73) Assignee: Yur Inc., San Mateo, CA (US)

( * ) Notice: Subject to any disclaimer, the term of this patent is extended or adjusted under 35 U.S.C. 154(b) by 0 days.

(21) Appl. No.: 17/025,694

(22) Filed: Sep. 18, 2020

(65) Prior Publication Data

US 2021/0085219 A1 Mar. 25, 2021

Related U.S. Application Data

(60) Provisional application No. 62/903,259, filed on Sep. 20, 2019.

(51) Int. Cl.
*A61B 5/00* (2006.01)
*A61B 5/11* (2006.01)
(Continued)

(52) U.S. Cl.
CPC ............ *A61B 5/1114* (2013.01); *A61B 5/002* (2013.01); *A61B 5/0022* (2013.01); *A61B 5/024* (2013.01);
(Continued)

(58) Field of Classification Search
CPC ....... A61B 5/1114; A61B 5/742; A61B 5/117; A61B 5/024; A61B 5/002; A61B 5/0022;
(Continued)

(56) References Cited

U.S. PATENT DOCUMENTS

| | | | |
|---|---|---|---|
| 8,892,481 B2 * | 11/2014 | Landers | G06N 5/048 600/587 |
| 10,595,776 B1 | 3/2020 | Selvaraj et al. | |

(Continued)

FOREIGN PATENT DOCUMENTS

WO 2015060894 A1 4/2015

OTHER PUBLICATIONS

Final Office Action in related U.S. Appl. No. 17/145,853, dated Jun. 7, 2023.
(Continued)

*Primary Examiner* — May A Abouelela
(74) *Attorney, Agent, or Firm* — Scale LLP

(57) ABSTRACT

A mechanism for interpreting spatiotemporal data from augmented and virtual reality devices into fitness related metrics and recommendations. Spatiotemporal data can be compared to the physical data of the end user to interpret energy expense such as estimated calorie burn. A virtual reality or augmented reality device can report positional data over time as the user engages with a corresponding environment. The positional data is compared to a biometric profile of the end user to understand how their physical body is exerting itself. The spatiotemporal data is a series of coordinate data expressed over time. The biometric data is the physical profile of the end user. This data is used to understand and quantify physical movement while using a virtual reality or augmented reality device. The energy expense determination mechanism can be used to provide a virtual coach for activities and workouts, games involving physical movement, and other applications.

24 Claims, 17 Drawing Sheets

(51) Int. Cl.
  *A61B 5/117* (2016.01)
  *G06F 3/01* (2006.01)
  *A61B 5/024* (2006.01)

(52) U.S. Cl.
  CPC .............. *A61B 5/117* (2013.01); *A61B 5/742* (2013.01); *G06F 3/011* (2013.01)

(58) Field of Classification Search
  CPC ... A61B 5/1118; A61B 5/1128; A61B 5/4866; G06F 3/011; G16H 20/30
  USPC .................................................. 600/587, 595
  See application file for complete search history.

(56) References Cited

U.S. PATENT DOCUMENTS

| | | | |
|---|---|---|---|
| 10,825,318 B1 | 11/2020 | Williams et al. | |
| 2014/0276119 A1 | 9/2014 | Venkatraman et al. | |
| 2014/0307927 A1* | 10/2014 | Folmer | A61B 5/4866 382/107 |
| 2015/0092980 A1* | 4/2015 | Folmer | G06V 40/165 382/103 |
| 2016/0086500 A1 | 3/2016 | Kaleal, III | |
| 2016/0220867 A1* | 8/2016 | Flaherty | G16H 20/30 |
| 2017/0004358 A1* | 1/2017 | Bose | G06K 9/0053 |
| 2018/0085630 A1* | 3/2018 | Capell | A63B 24/0062 |
| 2018/0160943 A1* | 6/2018 | Fyfe | A61B 5/14542 |
| 2019/0076037 A1* | 3/2019 | Bharati | A61B 5/7275 |
| 2019/0091515 A1* | 3/2019 | Shavit | G06F 3/017 |
| 2019/0138696 A1* | 5/2019 | Carpenter | G16H 40/67 |
| 2019/0206538 A1* | 7/2019 | Xing | G06Q 20/3829 |
| 2019/0251858 A1* | 8/2019 | Baharav | G16H 20/00 |
| 2019/0320920 A1* | 10/2019 | Orvis | A61B 5/0205 |
| 2019/0339849 A1* | 11/2019 | Williams | G06F 3/0483 |
| 2020/0009444 A1* | 1/2020 | Putnam | H04N 21/44029 |
| 2020/0047027 A1* | 2/2020 | Ward | A63B 24/0021 |
| 2020/0245928 A1* | 8/2020 | Kang | A61B 5/486 |
| 2022/0218209 A1 | 7/2022 | Shah et al. | |

OTHER PUBLICATIONS

Non-Final Office Action in related U.S. Appl. No. 17/145,853, dated Oct. 28, 2022.

* cited by examiner

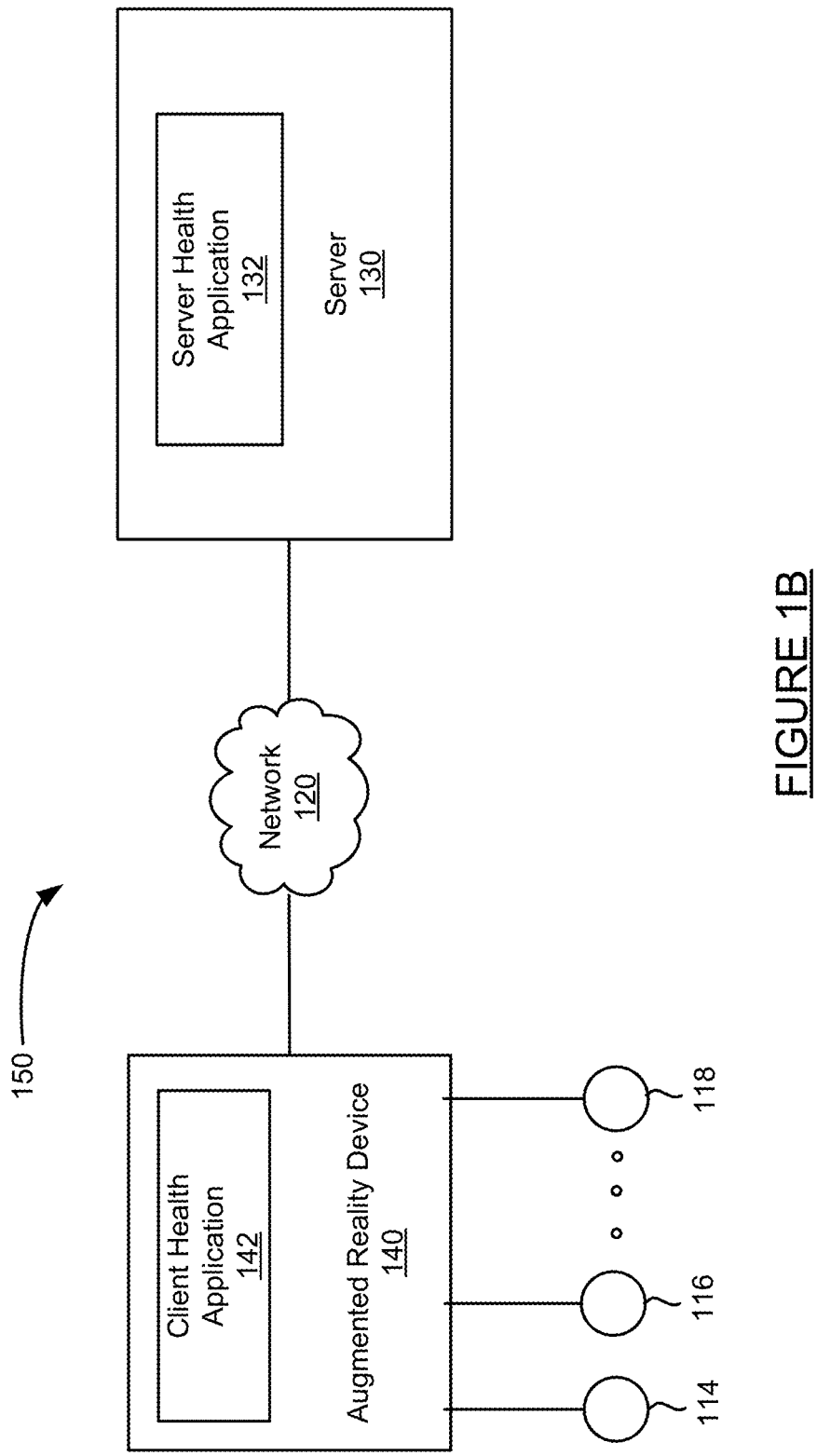

ENERGY EXPENSE DETERMINATION FROM SPATIOTEMPORAL DATA

CROSS REFERENCE TO RELATED APPLICATIONS

The present application claims the priority benefit of U.S. provisional patent application No. 62/903,259, filed on Sep. 20, 2019, titled "Energy Expense Determination From Spatial Temporal Data," the disclosure of which is incorporated herein.

SUMMARY

The present technology, roughly described, provides a mechanism for interpreting spatiotemporal data from augmented reality devices and virtual reality devices into fitness related metrics and recommendations. Spatiotemporal data can be compared to the physical data of an end user to interpret estimated energy expense (e.g., calorie burn or Joules) and quantifying fitness metrics (e.g., Squats). A virtual reality or augmented reality device can receive positional data from one or more position tracking sensors over time as the user engages in an activity, for example with a corresponding environment. The positional data is compared to a biometric profile of the end user to understand how their physical body is exerting itself. The spatiotemporal data is a series of coordinate data expressed over time. The biometric data is the physical profile of the end user. This data is used to understand and quantify physical movement while using a virtual reality or augmented reality device.

The present technology does not use a heart rate monitor to determine energy expense from the user. Rather, user energy expense is determined from user motions, captured from motion sensors in communication with a virtual, augmented, or other device, metadata, and from user biometric data. By not requiring a heart rate monitor, the user can enjoy activities, challenges, workouts, or other physical assertion without being inconvenienced with wearing a device that must be positioned to record heart rate data.

In some instances, a method for automatically determining the calories burned by a user during a workout. The method begins with receiving spatiotemporal data by a client application, stored and executing on a client device. The client application includes a display for displaying activity elements associated with a user workout, and the spatiotemporal data indicates the spatial coordinates of a plurality of points associated with a user's body while the user is performing the work. The spatial data is received periodically to comprise spatiotemporal data. The method includes determining an estimated heart rate for the user while performing the workout. The heart rate can be determined based on the spatiotemporal data and user biometric data that does not change during the workout. The method also determines an energy expense for the user during the workout based on the spatiotemporal data and the estimated user heart rate. The method can display the energy expense by the user and the estimated heart rate for the user during the workout by the client application. The client application displays energy expense information with the activity elements within the display.

In some instances, a non-transitory computer readable storage medium includes embodied thereon a program, wherein the program is executable by a processor to perform a method for automatically determining the calories burned by a user during a workout. The method begins with receiving spatiotemporal data by a client application stored and executing on a client device. The client application includes a display for displaying activity elements associated with a user workout, and the spatiotemporal data indicates the spatial coordinates of a plurality of points associated with a user's body while the user is performing the working. The spatial data is received periodically to comprise spatiotemporal data. The method includes determining an estimated heart rate for the user while performing the workout. The heart rate can be determined based on the spatiotemporal data and user biometric data that does not change during the workout. The method also determines an energy expense for the user during the workout based on the spatiotemporal data and the estimated user heart rate. The method can display the energy expense by the user and the estimated heart rate for the user during the workout by the client application. The client application displays energy expense information with the activity elements within the display.

In some instances, a system can automatically determine the calories burned by a user during a workout. The system can include a server which includes a memory and a processor. One or more modules can be stored in the memory and executed by the processor to receive spatiotemporal data by a client application stored and executing on a client device, the client application including a display for displaying activity elements associated with a user workout, the spatiotemporal data indicating the spatial coordinates of a plurality of points associated with a user's body while the user is performing the working, the spatial data received periodically to comprise spatiotemporal data, determine an estimated heart rate for the user while performing the workout, the heart rate determined based on the spatiotemporal data and user biometric data that does not change during the workout, determine an energy expense for the user during the workout based on the spatiotemporal data and the estimated user heart rate, and display the energy expense by the user and the estimated heart rate for the user during the workout by the client application, the client application displaying energy expense information with the activity elements within the display.

BRIEF DESCRIPTION OF FIGURES

FIG. 1B is a block diagram of an energy expense determination system within an augmented reality device.

DETAILED DESCRIPTION

The present technology, roughly described, provides a mechanism for interpreting spatiotemporal data from augmented reality devices and virtual reality devices into fitness related metrics and recommendations. Spatiotemporal data can be compared to the physical data of an end user to interpret energy expense (e.g., estimated calorie burn or joules). A virtual reality or augmented reality device can receive positional data from one or more position tracking sensors over time as the user engages in an activity, for example with a corresponding environment. The positional data is compared to a biometric profile of the end user to understand how their physical body is exerting itself. The spatiotemporal data is a series of coordinate data expressed over time. The biometric data is the physical profile of the end user. This data is used to understand and quantify physical movement while using a virtual reality or augmented reality device.

The present technology does not use a heart rate monitor to determine energy expense from the user. Rather, user energy expense is determined from user motions, captured from motion sensors in communication with a virtual, augmented, or other device, and from user biometric data. By not requiring a heart rate monitor, the user can enjoy activities, challenges, workouts, or other physical assertion without being inconvenienced with wearing a device that must be positioned to record heart rate data.

The present technology can be used in a variety of applications. For example, the energy expense determination mechanism can be used to provide a virtual coach for activities and workouts, quantifying fitness movements (e.g., squats), games involving physical movement, and other applications. In some instances, motion tracking data captured for the user can be utilized, both in raw and processed form, to provide end-user specific physical recommendations in spatial environments through visual and/or audio cues.

Figure 1A:
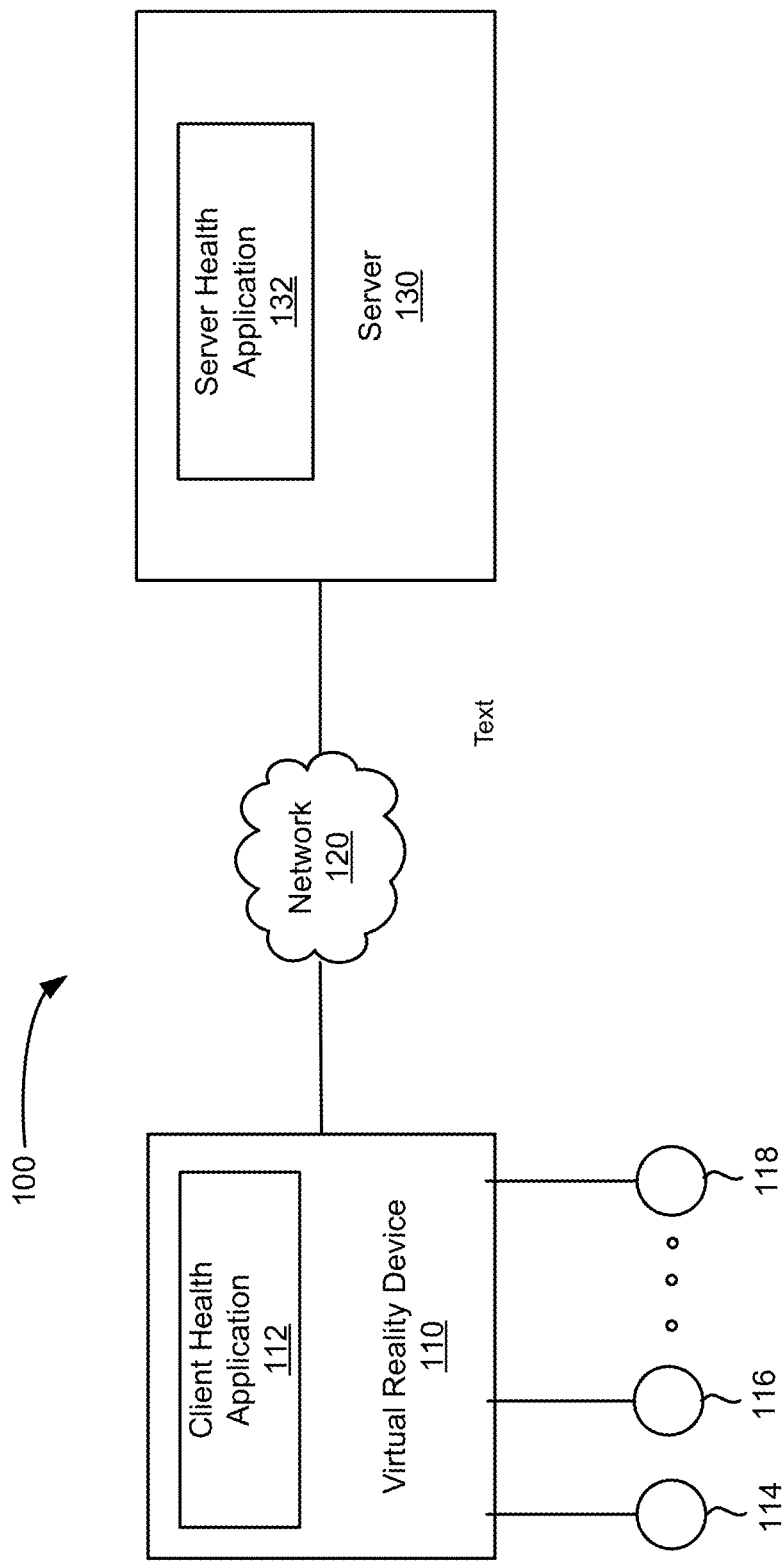
FIG. 1A is a block diagram of an energy expense determination system within a virtual reality device.

FIG. 1A is a block diagram of an energy expense determination system within a virtual reality device. System 100 of FIG. 1A includes virtual reality device 110, network 120, and server 130. Virtual reality device 110 may include one or more applications associated with a user performing a virtual activity in a virtual space. Virtual reality device 110 includes client health application 112 and receives data from motion tracking sensors 114, 116 and 118. Although three motion tracking sensors are illustrated, any number of motion tracking sensors may be used with the present technology.

Client health application 112 may be implemented as software and/or hardware on virtual reality device 110. In some instances, module 112 may be implemented as code that interfaces with the native system of virtual reality device 110. Client health application 112 may determine the energy expense of a user that utilizes virtual reality device 110 and may communicate with server 130 over network 120. In some instances, client health applications may analyze data, determine calories burned and energy expense, manage and update dashboards, generate notifications, detect events, and perform other functionality discussed herein Client health application 112 is discussed in more with respect to FIG. 1E.

Network 120 may include one or more private networks, public networks, intranets, the Internet, wide-area networks, local area networks, cellular networks, radiofrequency networks, Wi-Fi networks, and any other network which may be used to transmit data. Device 110 and server 130 may communicate over network 120.

Server 130 can be implemented on one or more logical or physical servers, as a single machine or distributed machines, and may communicate with virtual reality device 110 over network 120. Server 130 includes server health application 132, which may be a single application or several applications. Server health application 132 may communicate with client health application 112 on device 110 and may analyze data, determiner calories burned and energy expense, manage and update dashboards, generate notifications, detect events, and perform other functionality discussed herein. Server health application 132 is discussed in more detail with respect to FIG. 1F.

FIG. 1B is a block diagram of an energy expense determination system within an augmented reality device. The system of FIG. 1B is similar to that of FIG. 1A except that the device is an augmented reality device rather than a virtual reality device. As such, the client health application 142 may process images and video to provide graphics, text, video, and/or other content with the images and video. The images and video may be captured by a camera device local to an augmented reality device or remote from an augmented reality device. The server health application 132, client health application 142, sensors 144-148, network 120, and server 130 of FIG. 1B operate similarly to those described with respect to FIG. 1A.

Though a virtual reality device and augmented reality device are discussed with respect to FIGS. 1A and 1B, it is understood that other devices can be used with the present technology as well. For example, health module 142 can be contained in any device that receives motion tracking data from a number of sensors. The present technology is not intended to be limited to virtual reality and augmented reality devices.

Figure 1C:
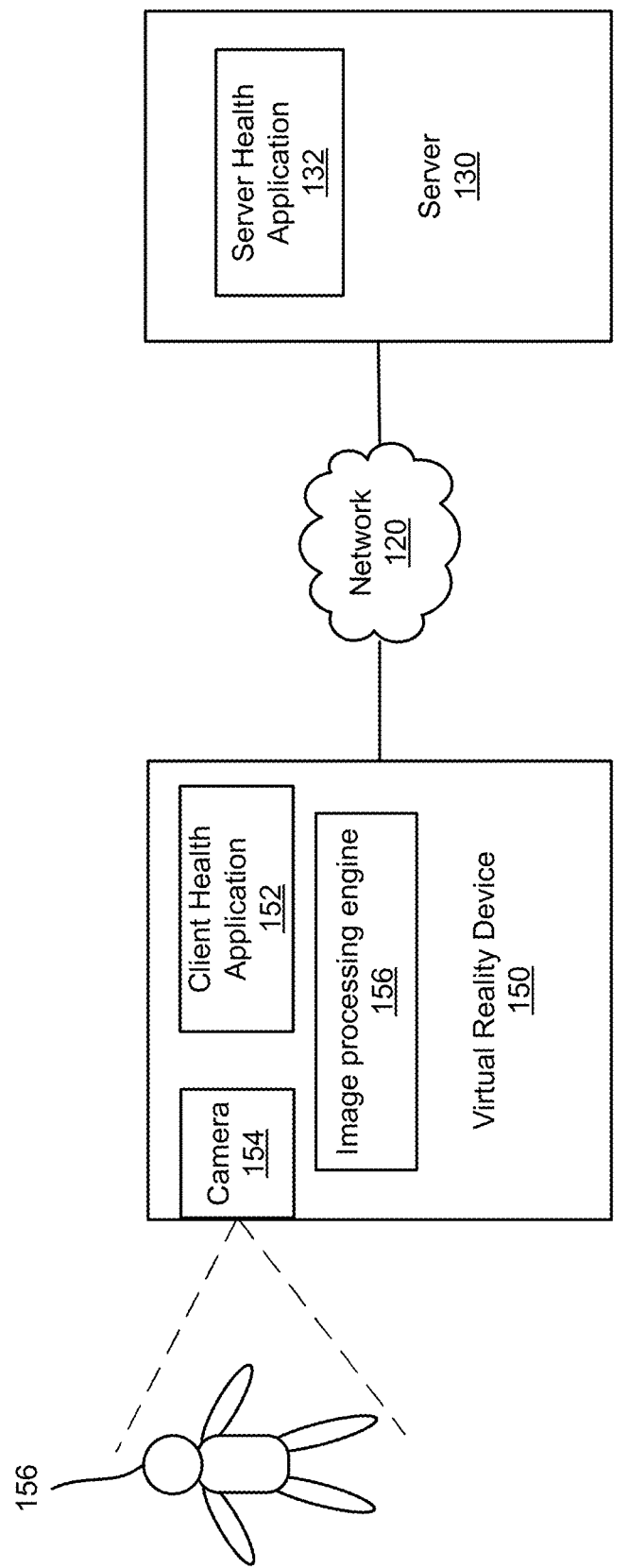
FIG. 1C is a block diagram of an energy expense determination system within an virtual reality device that processes spatiotemporal data determined from images.

FIG. 1C is a block diagram of an energy expense determination system within a virtual reality device that processes spatiotemporal data determined from images. The energy expense system of FIG. 1C is similar to the system of FIG. 1A except that the virtual reality device 150 includes a camera 154 and image processing engine 156. In some instances, the camera 154 may be a camera on a cellular telephone, a tablet computer, or some other computing device.

The camera may be any camera that is suitable for capturing images and/or video of a user. Image processing engine may process images captured by camera 154 to calculate points of inflection on a user, the position of the points in a three dimensional coordinate system, the velocity and angular velocity of each point over time, and other data. In some instances, positions in a two-dimensional system may be calculated and used in the present system. The image processing engine 156 may transmit the calculated data to client health application 152.

Figure 1D:
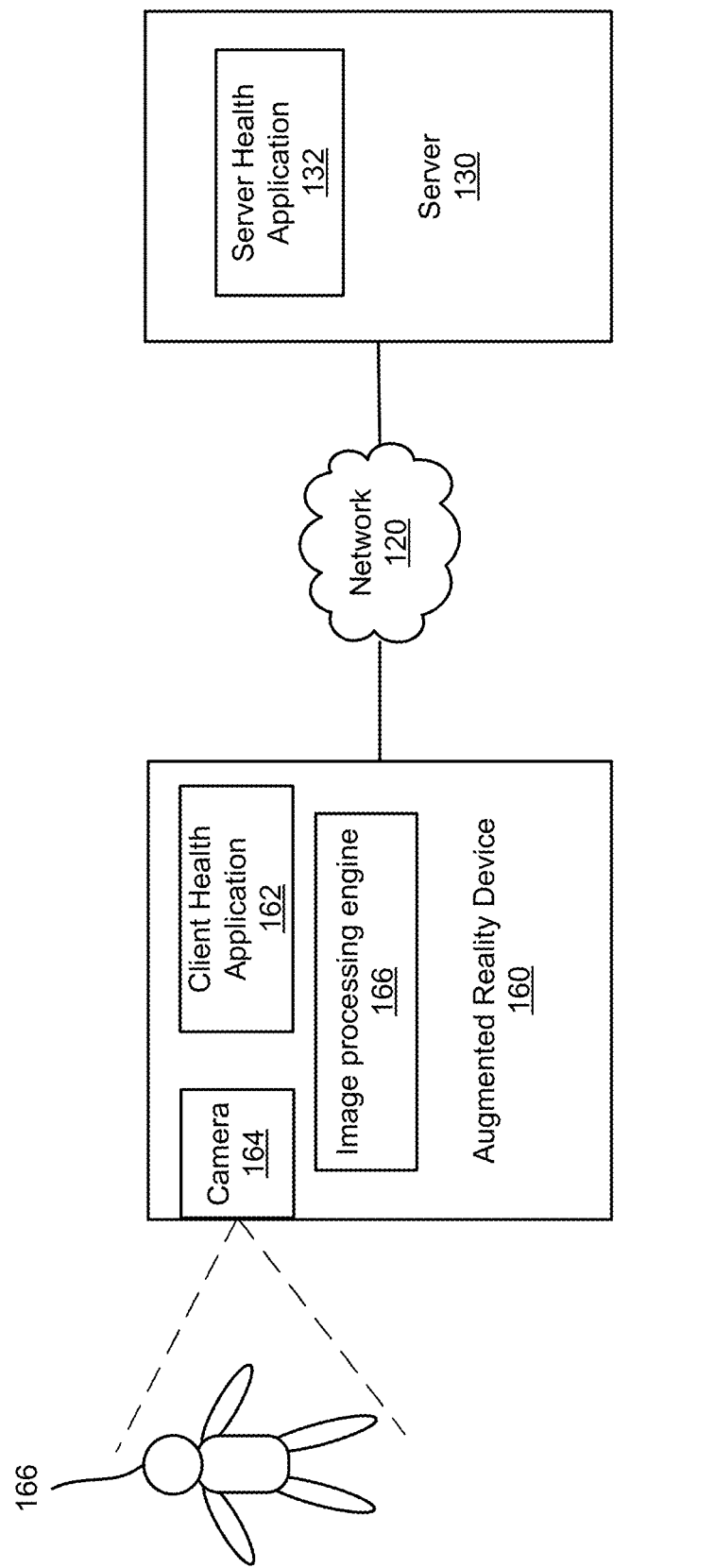
FIG. 1D is a block diagram of an energy expense determination system within an augmented reality device that processes spatiotemporal data determined from images.

FIG. 1D is a block diagram of an energy expense determination system within an augmented reality device that processes spatiotemporal data determined from images. The energy expense system of FIG. 1D is similar to the system of FIG. 1B except that the augmented reality device 160 includes a camera 164 and image processing engine 166. In some instances, the camera 164 may be a camera on a cellular telephone, a tablet computer, or some other computing device.

The camera 164 may be any camera that is suitable for capturing images and/or video of a user. Image processing engine may process images captured by camera 164 to calculate points of inflection on a user, the position of the points in a three dimensional coordinate system, the velocity and angular velocity of each point over time, and other data. In some instances, positions in a two-dimensional system may be calculated and used in the present system. The image processing engine 166 may transmit the calculated data to client health application 162.

Figure 1E:
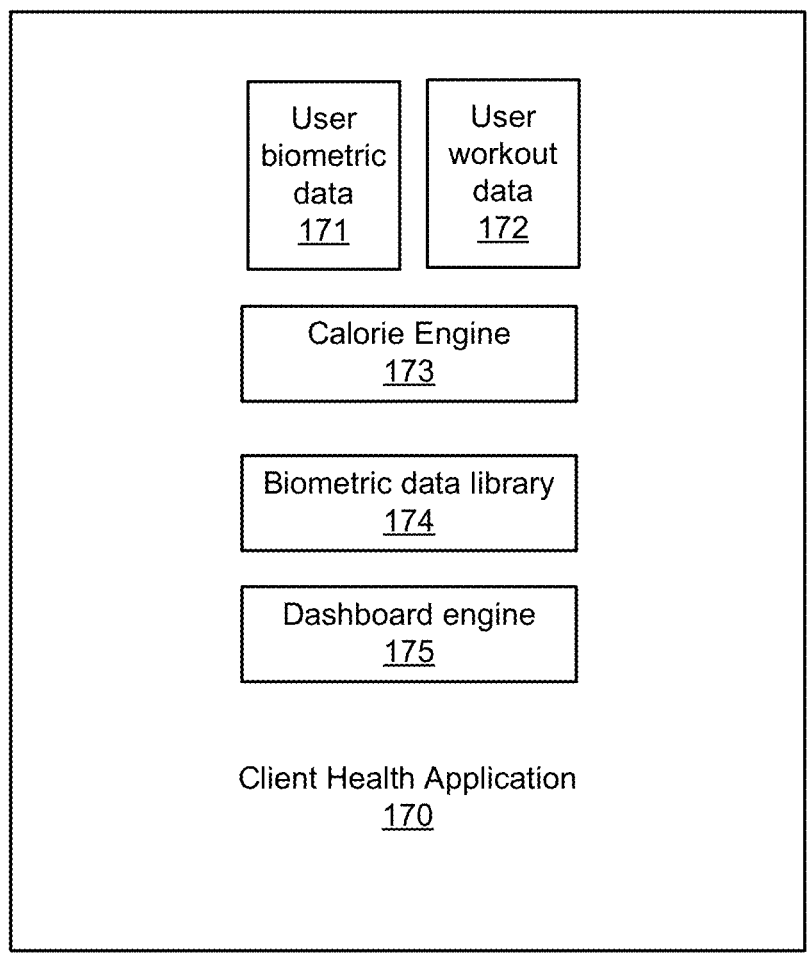
FIG. 1E is a block diagram of a client health application.

FIG. 1E is a block diagram of a client health application 170. The client health application 170 provides more detail for the client health applications of FIGS. 1A-1D. Client health application 170 includes user biometric data 171, user workout data 172, calorie engine 173, biometric data library 174, and dashboard engine 175. User biometric data 171 may include biometric details for the user, such as a height, weight, date of birth, body mass index, lean body mass data, water percentage, and other data. User workout data 172 may include details for one or more workout segments for the user. In some instances, a workout segment includes details for a particular workout characterized by a start time, end time, and other data.

Calorie engine 173 may analyze spatiotemporal data, determine a calculation method, determine calories burned and/or energy expense, and perform other functionality described herein.

Biometric data library 138 includes data obtained from the current user and/or other users relating to motion tracking data and a corresponding energy expense associated with the data. In some instances, client health application 170 may compare captured user motion tracking data and biometric data to the biometric data library in order to determine an energy expense for the user's corresponding motion tracking data.

Dashboard engine 175 may calculate metrics, retrieve information to be populated into a dashboard, update a dashboard, and transmit dashboard data to a remote application for display.

Figure 1F:
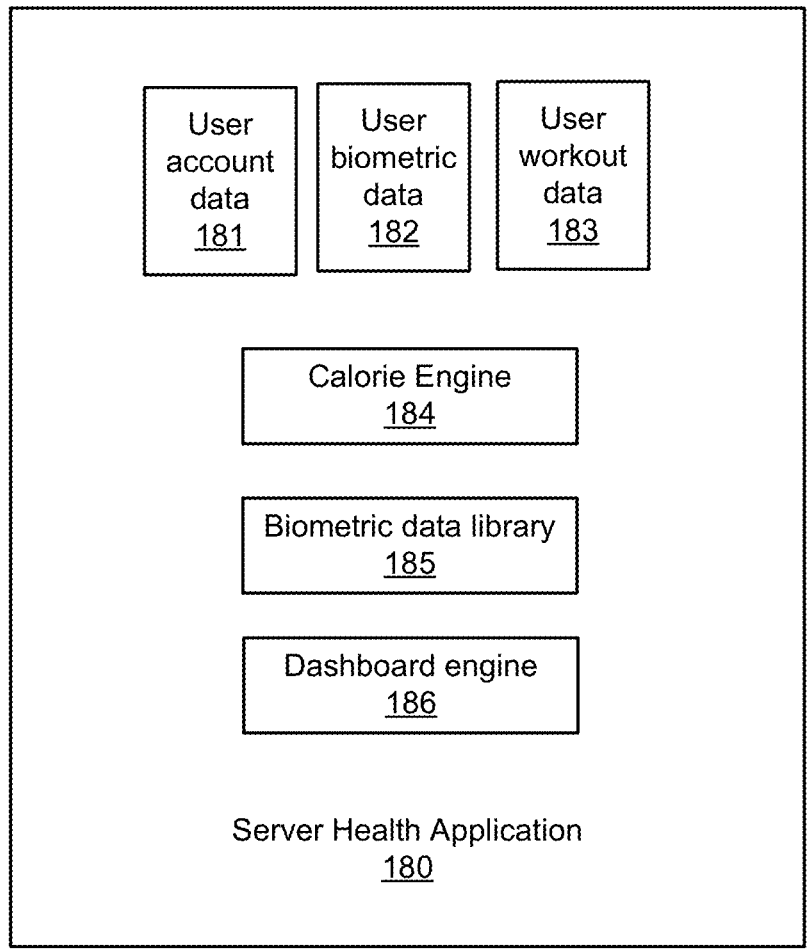
FIG. 1F is a block diagram of a server health application.

FIG. 1F is a block diagram of server health application 180. The server health application 180 provides more detail for the client health applications of FIGS. 1A-1D. Server health application 180 includes user account data 181, user biometric data 182, user workout data 283, calorie engine 184, biometric data library 185, and dashboard engine 186. User account data includes data associated with a user's account with the system, such as but not limited to username, password, PIN, and other information.

User biometric data 182 may include biometric details for the user, such as a height, weight, date of birth, body mass index, lean body mass data, water percentage, and other data. User workout data 183 may include details for one or more workout segments for the user. In some instances, a workout segment includes details for a particular workout characterized by a start time, end time, and other data.

Calorie engine 184 may analyze spatiotemporal data, determine a calculation method, determine calories burned and/or energy expense, and perform other functionality described herein.

Biometric data library 185 includes data obtained from the current user and/or other users relating to motion tracking data and a corresponding energy expense associated with the data. In some instances, server health application 180 may compare captured user motion tracking data and biometric data to the biometric data library in order to determine an energy expense for the user's corresponding motion tracking data.

Dashboard engine 186 may calculate metrics, retrieve information to be populated into a dashboard, update a dashboard, and transmit dashboard data to a remote application for display.

Figure 2:
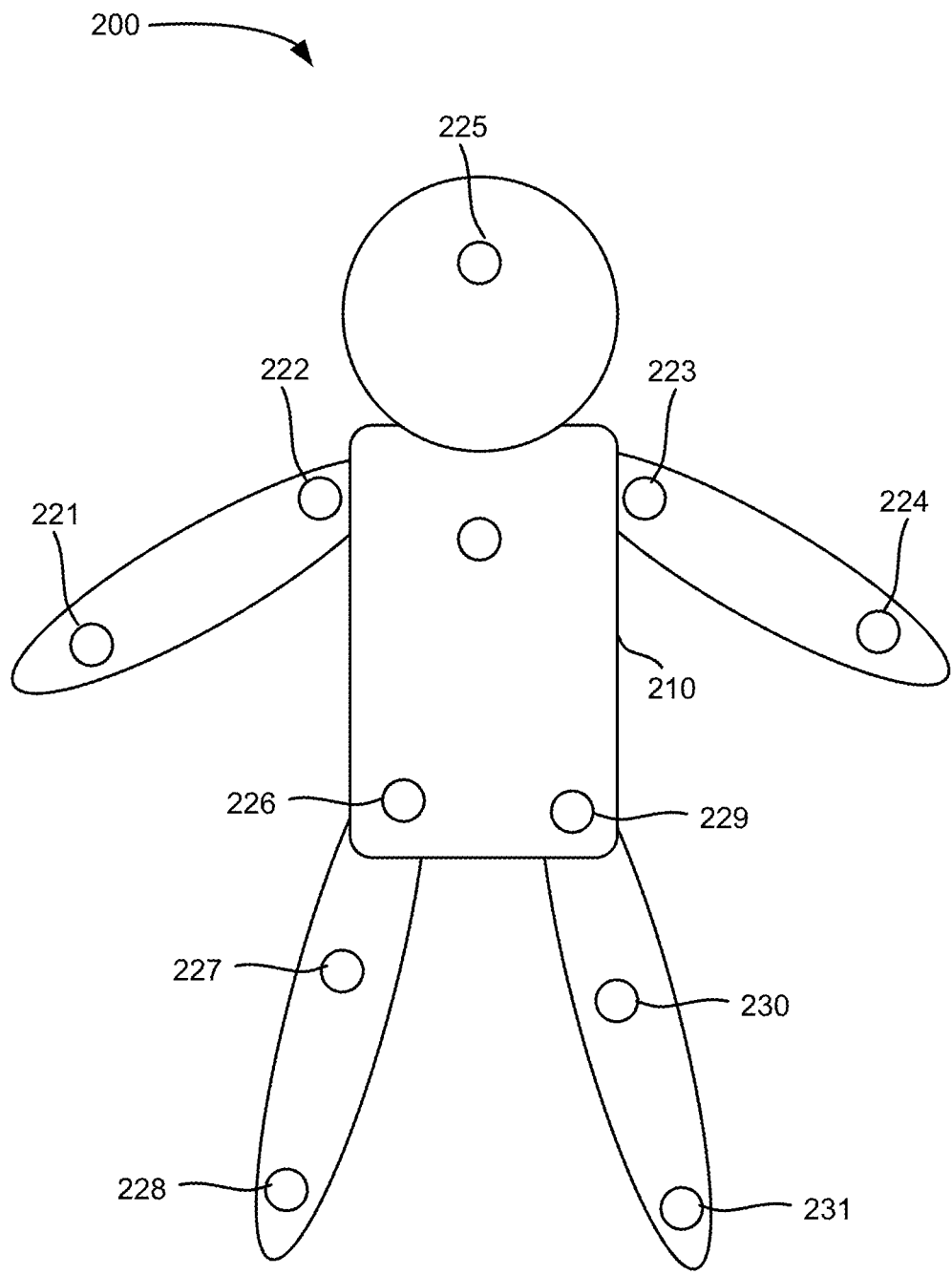
FIG. 2 is a block diagram of motion tracking data capture and transmission devices.

FIG. 2 is a block diagram of motion tracking data capture and transmission devices. In FIG. 2, a user 210 may be fitted with one or more motion tracking data capture and transmission devices 221-231. As shown in FIG. 2, exemplary devices 221-231 may be placed on the user. In some instances, the devices may be placed on a user's arm, feet, body, head, and other locations. Though eleven devices are illustrated on a user in FIG. 2, any number of devices may be implemented, for example 20, 30, 40, 50, or any other number. For purposes of discussion, the present technology may be discussed with respect to sensors 221 and 224 on the user's arms and sensor 225 on a user's head.

Figure 3:
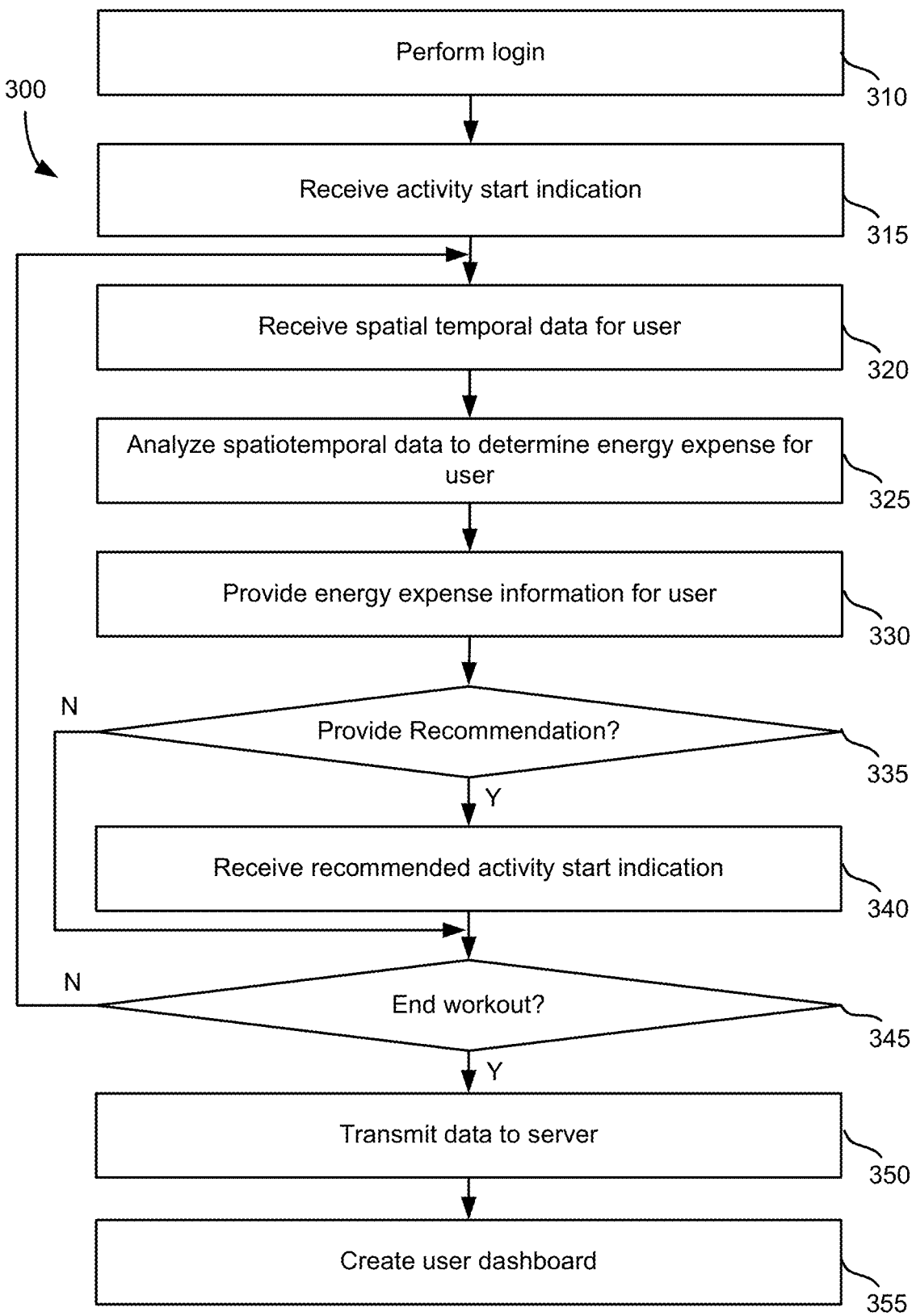
FIG. 3 is an exemplary method for determining energy expense for a user.

FIG. 3 is an exemplary method for determining energy expense for a user. First, login is performed at step 310. A user may login to one or more applications on a virtual reality or augmented reality device as well as software associated with the present technology. Login is discussed in more detail with respect to the method of FIG. 4.

An activity start indication is received at step 315. In some instances, the activity start indication may be the start of an application installed on a virtual reality or augmented reality device, such as an exercise application, physical therapy application, game application, or some other application that provides a physical workout, challenge, activity, or other physical experience. The indication may signify that a user play or experience space has been established for the user within a virtual or augmented reality space with a third-party application, and that the user is now able to engage in an activity.

In some instances, the indication may include detection of an application start which has components associated with VR or AR. For example, code may be implemented on the client device to detect when the operating system starts an application having a camera or other component that is suitable with or commonly associated with VR or AR functionality.

Spatiotemporal data is received for a user at step 320. The spatiotemporal data can include data derived or generated from one or more images or motion tracking data. Data generated from one or more images or video can be generated after performing image analysis techniques on a series of images or video in which the user is performing the workout. Image processing software may receive the images and video, process the changing position of the user in the series of images and/or video, and determine the user joints, degree of movement, and location of the user's body in a three dimensional (or two dimensional) coordinate system. The image processing software may be implemented by a system operation system, client health application, server health application, or other software and/or hardware used within or communication with the present system.

In the case of motion tracking data, the motion tracking data is received from one or more motion tracking sensors placed on the user's body. The data may be received wirelessly or via wired connections. In some instances, the motion tracking data may be sampled periodically, such as for example between 60 to 100 Hz by the device 110 or 140.

In some instances, there are three tracked points on a user—a tracking point on the head of a user, for example attached a tracking point on a headset worn by a user, and a tracking point at each hand of the user, for example a tracking mechanism attached to a glove, other user clothing, or directly attached to the user's hand. As a result of the three tracking points, the motion tracking data can include position information for each of the three points, providing six degrees of freedom for each point. In this example, physical estimates of the tracking point locations, velocity, and/or overall body mechanics and activity can be determined from the motion tracking data received for the three tracked points in six degrees of freedom.

In some instances, the origin of the received motion tracking data is irrelevant. Hence, motion tracking data can be obtained from motion tracking devices placed on a user, a device with a camera such as a cellular phone, or some other device or series of devices. Receiving motion tracking data from a device with a camera is discussed with respect to FIG. 5. Receiving motion tracking data from one or more motion tracking devices is discussed with respect to FIG. 6.

Spatiotemporal data can be analyzed to determine an energy expense for a user at step 325. Energy expense may be determined at least in part from the Spatiotemporal data captured during activity performed by the user. More details for analyzing Spatiotemporal data to determine energy expense for a user is discussed with respect to the method of FIG. 7.

Energy expense information may be provided for the user at step 330. The energy expense information may include calories burned during the current activity. A determination is then made as to whether a recommendation should be provided at step 335. A recommendation may be provided based on several factors, such as for example whether an intended duration of the current activity is completed, whether a goal number of calories have burned, or some other event, such as for example if a user is performing poorly in a current activity based on an analysis of the motion tracking data. If a recommendation should not be provided, the method of FIG. 3 continues to step 345. If a recommendation should be provided, the recommendation is provided at step 340, wherein an activity start indication for the recommended activity is received. The recommendation may include execution of a different application, such as for example an application that is more difficult or easier than the previous application, a particular activity within an application, or visual cues of activity within the present executed application.

A determination is made at step 345 as to whether the workout should be terminated. Workouts can end if the particular activity, challenge, or game is complete, if the executing application terminates, if there is a pause in user activity or the game itself for a certain period of time, such as at least one minute. If the workout should not end, the method returns to step 320 where motion tracking data is received for a user. If the workout has come to an end, then data is transmitted to a server at step 350. The data transmitted may include spatiotemporal data collected by the client device, user input received by the client device, and other data. Once data is transmitted to the server, the server may create a user dashboard at step 355. The user dashboard may be configured by a user and provide information regarding the user workout. More details for creating a dashboard are discussed with respect to FIG. 9.

Figure 4:
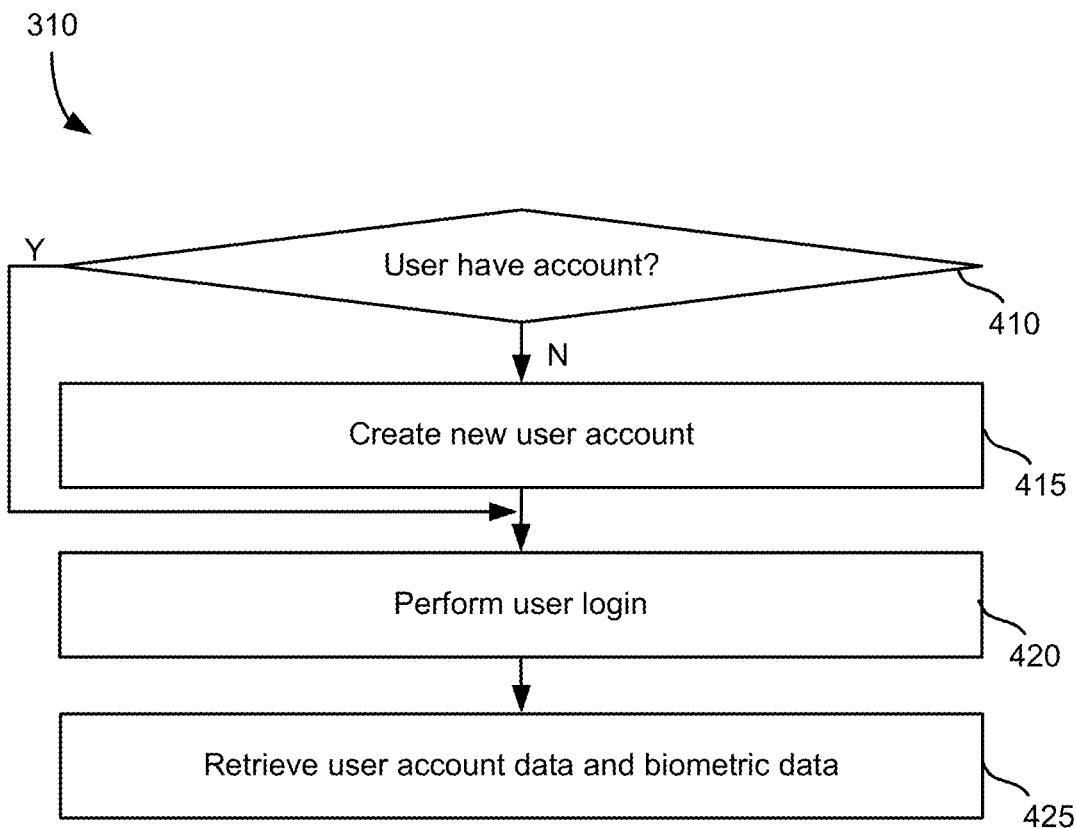
FIG. 4 is an exemplary method for performing login for a user.

FIG. 4 is an exemplary method for performing login for a user. In some instances, the method of FIG. 4 provides more detail for step 310 the method of FIG. 3. A determination is made as to whether a user has an account at step 410. If the user does have an account, the method continues to step 420. If the user does not have an account, a new account is created for the user at step 415. Creating a new account can include receiving user login information, user contact data, and other user data. A user may perform login by providing a username and password, or other credentials, at step 420. After user login has been confirmed, user account data and user biometric data retrieved at step 425. User account data may include the user's name. User biometric data may include a user's height, weight, birth date, body mass index, and other biometric data associated with the user.

Figure 5:
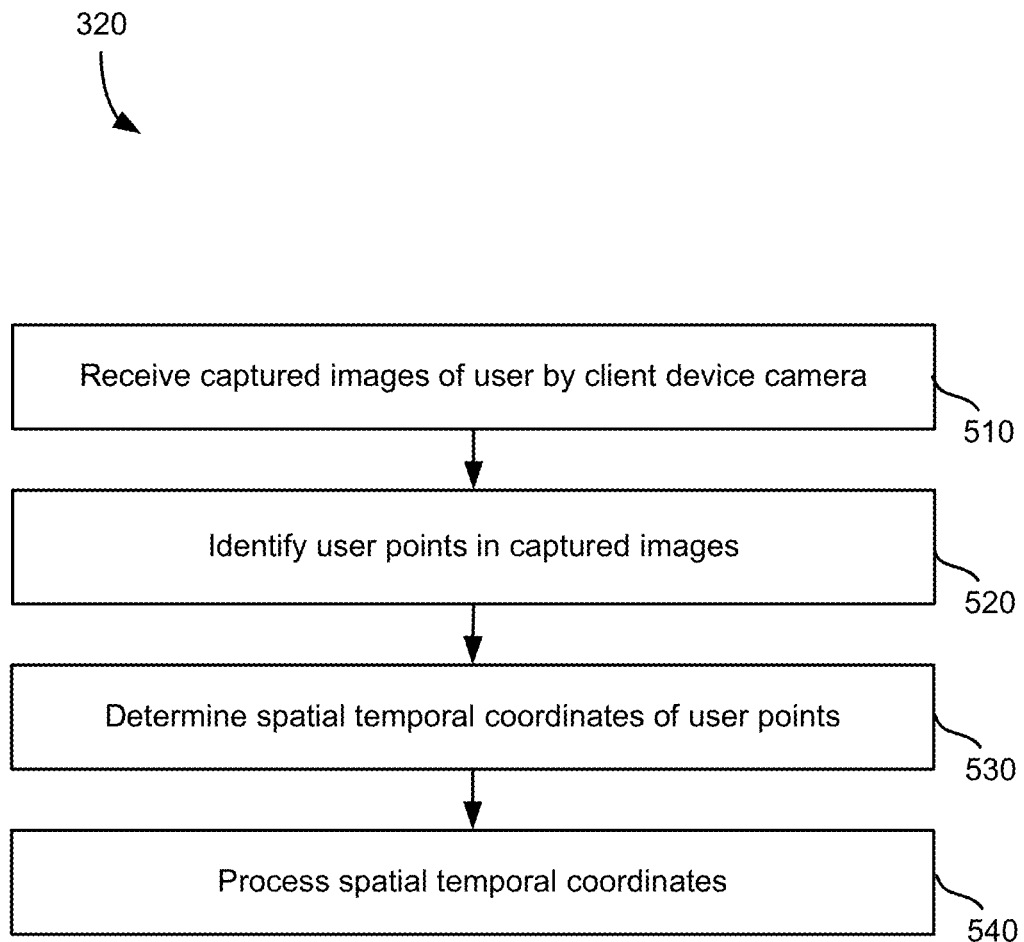
FIG. 5 is an exemplary method for receiving motion tracking data obtained by a client device camera.

FIG. 5 is an exemplary method for receiving motion tracking data obtained by a client device camera. Captured images of a user during a workout are captured by a client device camera at step 510. User points are identified in the captured images and/or video at step 520. The user points may be determined as points on the user body that move, points of body joints, and other points. Spatiotemporal coordinates of the user points may be determined at step 530. Hence, all the points are placed into a single spatiotemporal coordinate system that has three (ins some instances, two) spatial dimensions. The spatiotemporal coordinates are then processed to determine the movements of the user 540. For example, the coordinates may be processed to determine if a user is moving their arms or legs, swinging an object in their hands, doing an exercise or action such as jumping or running, and so forth.

Figure 6:
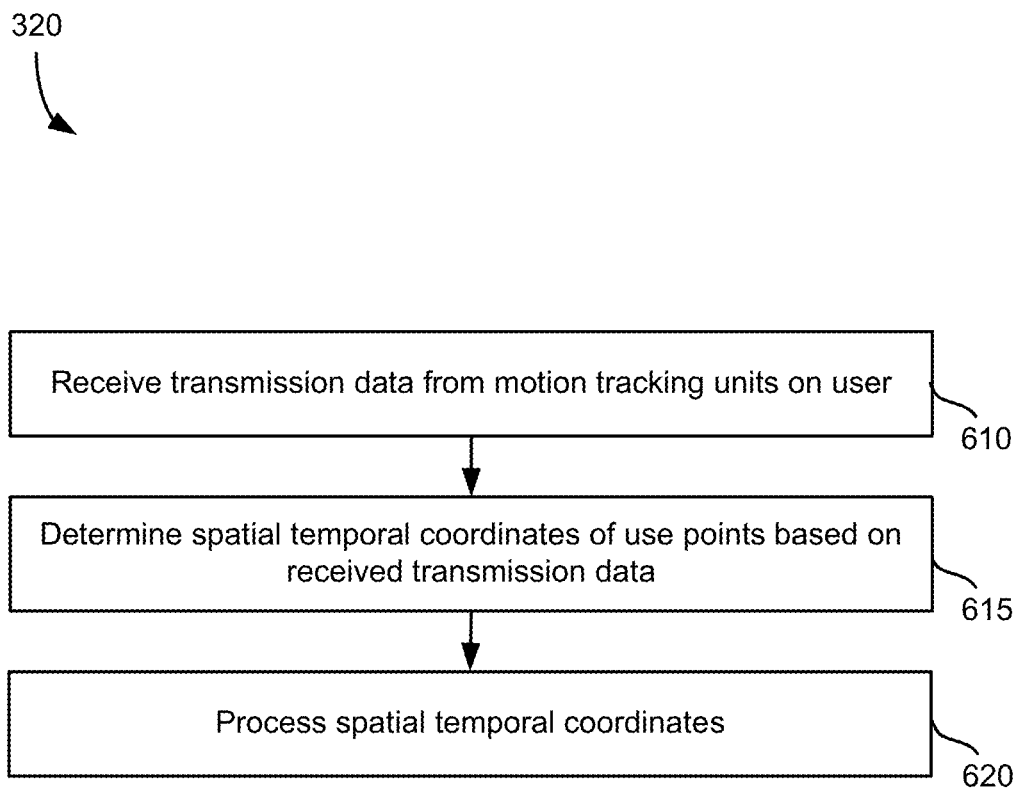
FIG. 6 is an exemplary method for receiving motion tracking data obtained from transmission units on a user.

FIG. 6 is an exemplary method for receiving motion tracking data obtained from transmission units on a user. Transmission data is received from motion tracking units on the user at step 610. Spatiotemporal coordinates of the user points may be determined based on the transmission data at step 615. The points are placed into a single spatiotemporal coordinate system that has three (in some instances, two) spatial dimensions. The spatiotemporal coordinates are then processed to determine the movements of the user 620. For example, the coordinates may be processed to determine if a user is moving their arms or legs, swinging an object in their hands, doing an exercise or action such as jumping or running, and so forth.

Figure 7:
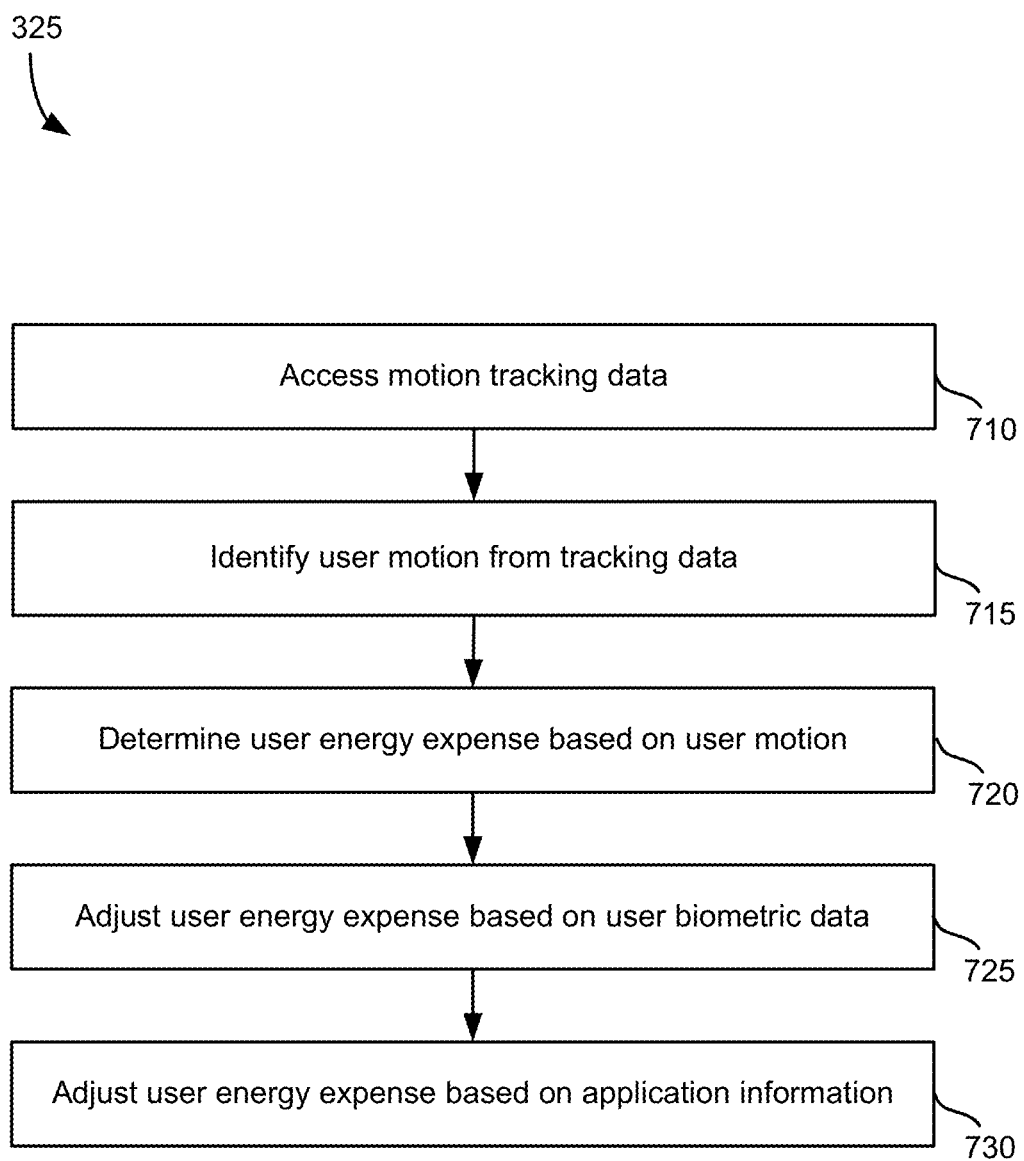
FIG. 7 is an exemplary method for analysing and processing motion tracking data.

FIG. 7 is an exemplary method for analysing and processing motion tracking data. The method of FIG. 7 provides more detail for step 325 of the method of FIG. 3. First, motion tracking data is accessed at step 710. The motion tracking data may include data captured over a set period of time, such as one second, two seconds, 0.5 seconds, or some other period of time. User motion is identified from the tracking data at step 715. The user identified motion may include swinging arms forward, lifting arms up, raising ahead, jumping, or some other user motion. User energy expense is determined based on user motion at step 720. In some instances, determining a user energy expense includes first determining a base energy expense, in some instances based in part on a resting energy expense. A resting energy expense may be determined is 3.5 J/millimetre/kilogram.

A user energy expense is adjusted based on user biometric data at step 725. The adjustment based on a user biometric data may include using a user's body mass index (BMI) to customize the energy expense for the particular user. For example, a user with a higher BMI will have a higher energy expense will user with a lower BMI will have a lower energy expense for a particular activity.

The user's energy expense can be adjusted based on application information at step 730. In some instances, when it is known would application a user is engaged with, the application can specify a particular activity the user is engaged in. For example, an application may indicate to the present technology that the user is engaged in squats, walking, sitting, running, or some other activity. In some instances, an activity by a user may appear to require very strenuous activity, and user controllers that appear to be moving very rapidly. However, the user may be moving the controllers by flicking their wrists rather than swinging their arms, and the actual calories spent will be less. In this case, user energy expense would be reduced, slightly. The specifics of activity which are received from application can be used to better to and futures energy expense over a set period of time.

Figure 8:
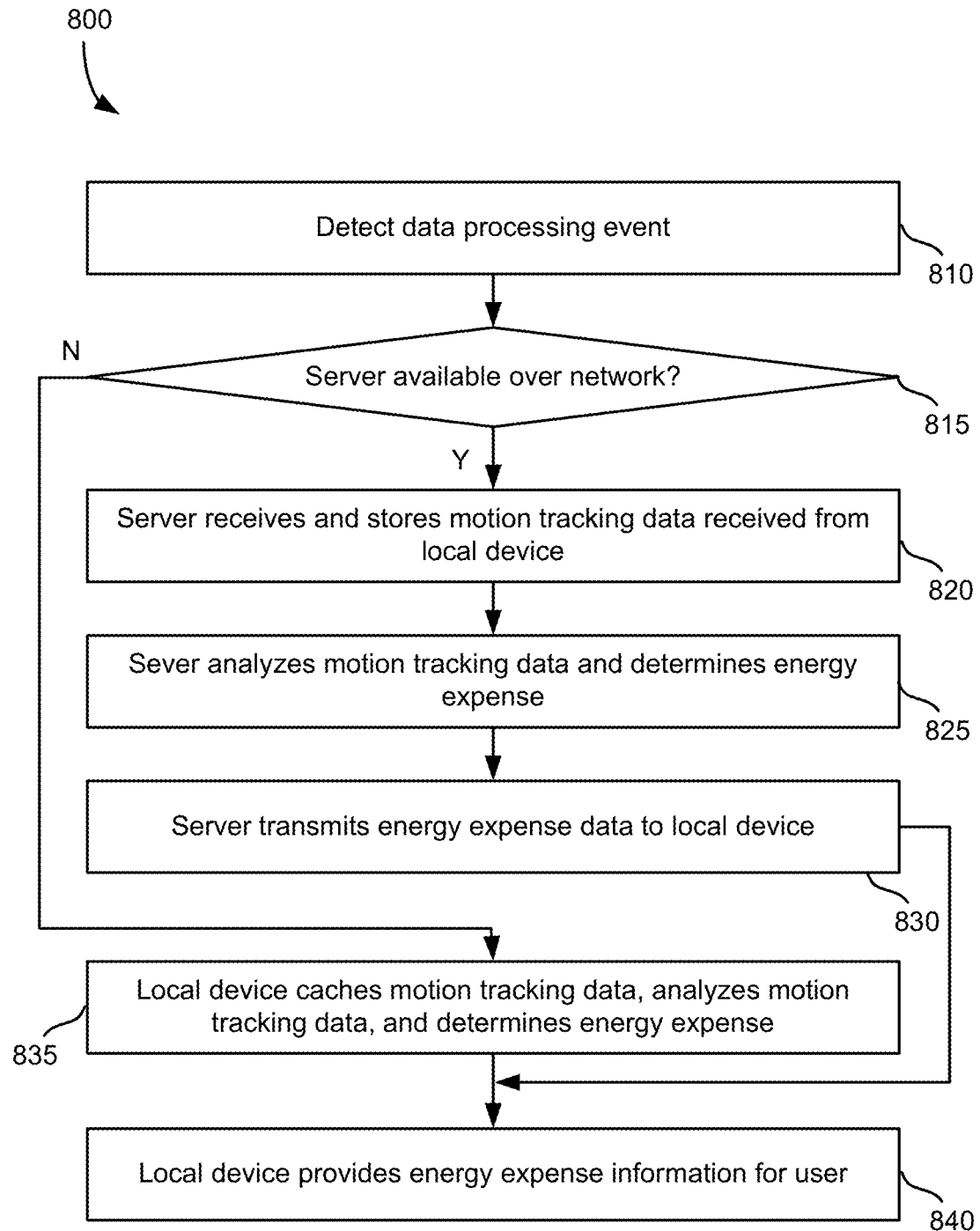
FIG. 8 is an exemplary method for reporting data to a server from a client.

In some instances, a client device collects data during a workout and repeatedly uploads the data to a server over a network. In some instances, the server or network may not be accessible. As such, the client device may store data locally until the server communication is established. FIG. 8 is an exemplary method for reporting data to a server from a client. A data processing event is detected at step 810. In some instances, the event is detected at the client, such as an event triggered to transmit collected workout data from the client to the server. A determination is made as to whether the server is available over a network at step 815. In some instances, the server is available if the client device can connect with the server device over the network. If the server is available, the server may process the motion tracking and other data collected by the client device, and the motion tracking data and other data is transmitted to the server by the client device. The server receives and stores the motion tracking data received from the local device at step 820. The server analyses the motion tracking data and determines an energy expense at step 825. The server then transmits the energy expense data to the local device at step 830. The client device (local device) receives the energy expense data, including calories burned data, and provides the energy expense information to the user at step 840. The energy expense can be displayed to the user through an overlay that is displayed during the user workout.

If, at step 815, the server is not available, the client device may perform calculations locally and store data in a local cache until a server connection can be established. At step 835, the client device caches motion tracking data, analyses motion tracking data, and determines the energy expense associated with the user workout.

Figure 9:
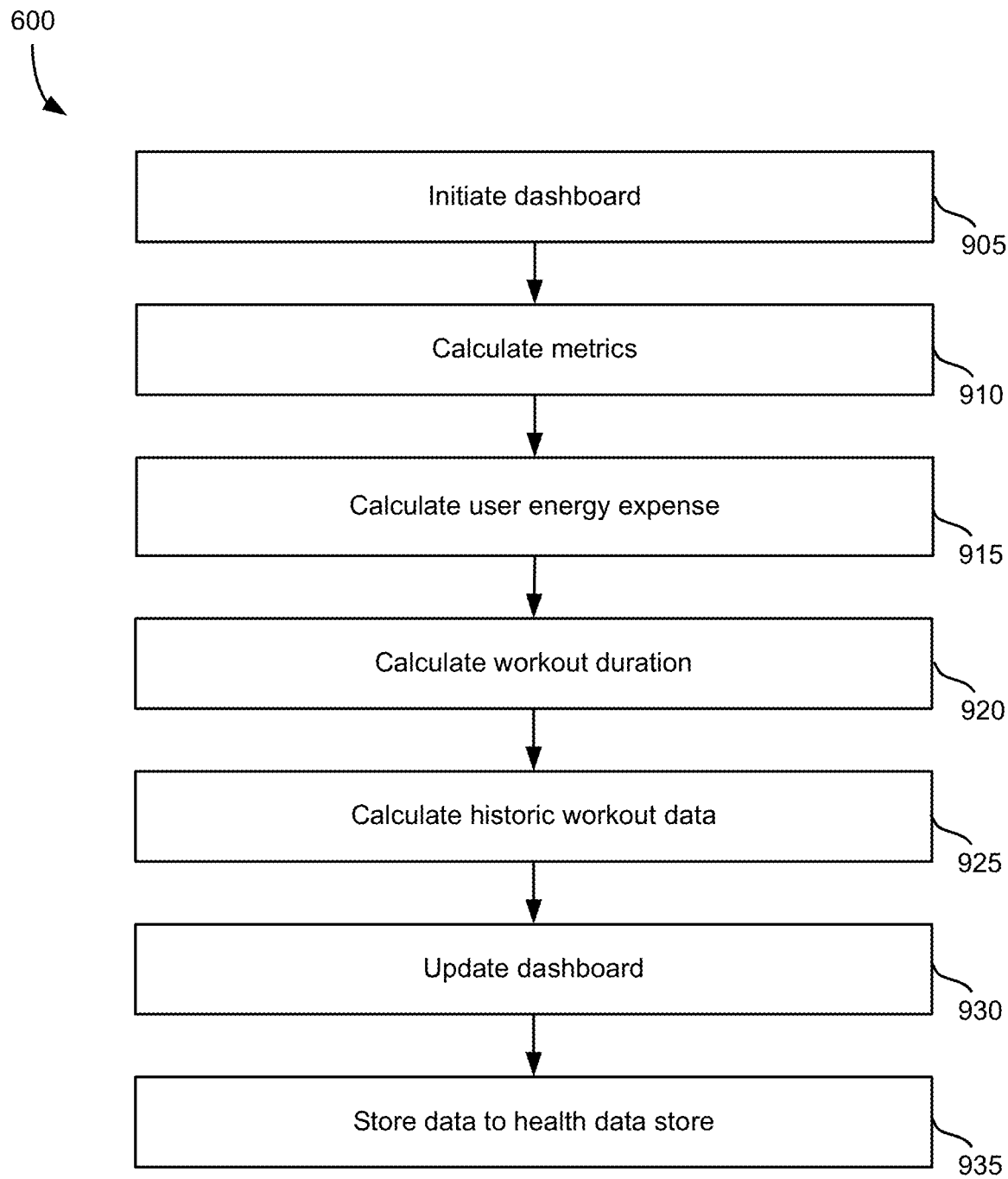
FIG. 9 is an exemplary method for providing a dashboard.

FIG. 9 is an exemplary method for providing a dashboard. The method of FIG. 9 provides more detail for step 355 of the method of FIG. 3. First, a dashboard is initiated at step 910. The dashboard may be initiated by generating a dashboard instance.

Metrics are calculated at step 910. The metrics may include workout metrics such as the average calories burned per minute, average calories burned per song, the length of the workout, the total calories burned, and other metrics. A user energy expense is updated at step 915. User energy expense may be updated in real time as user exercises and the updated energy expense is calculated. Workout duration may be updated at step 920. Historic workout data may be displayed and updated at step 925. Historic workout data may indicate the types of activities, duration, and calories burned for segments of workouts. Data from the dashboard can be stored to a health data store at step 930. A health data store may include a database, a library of data accessed by a health application, such as "Google Fit" or "Apple Health"

mobile applications, or some other electronic health record. The dashboard can then be updated based on the calculations between step 910-925. Updating the dashboard includes filling components of the dashboard with metrics calculated. The calculated data is then stored to a health data store.

Figure 10:
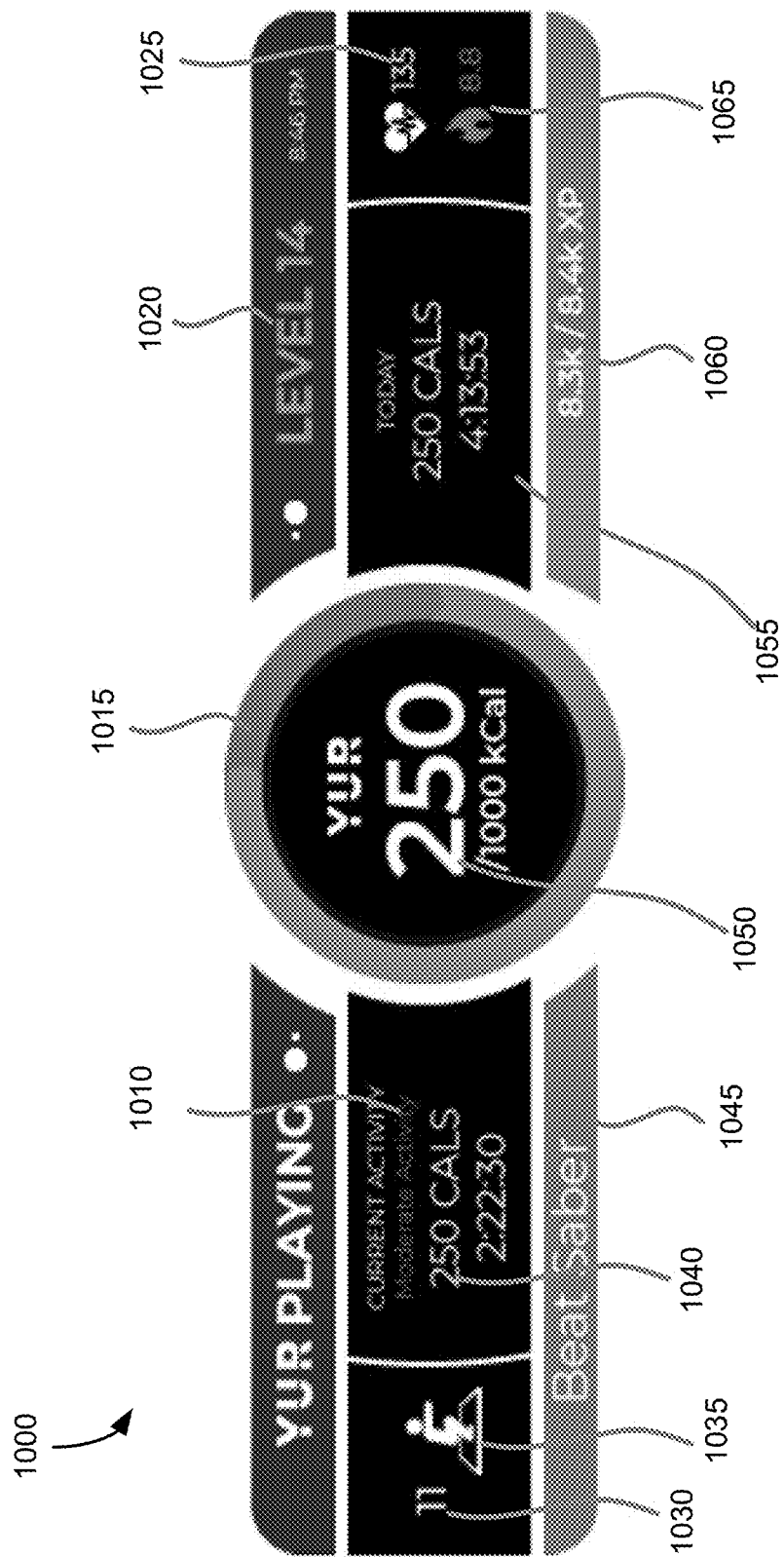
FIG. 10 is an exemplary overlay for use with a virtual reality device or augmented reality device.

FIG. 10 is an exemplary overlay 1000 for use with a virtual reality device or augmented reality device. The overlay 1000 may be displayed during a workout for a user during a virtual reality experience or augmented reality experience. The information in the overlay can be continuously updated, either from calculations calculated by a remote server and communicated to a local client device which provides the overlay or from calculations made by the local client which provides the overlay.

The overlay 1000 displays information such as a current activity level 1010, a levelling wheel 1015, level information 1020, estimated heart rate 1025, exercise counter 1030, exercise type graphic 1035, calories burned 1040, application name 1045, calories burned 1050, total calories burned in current day 1055, experience points 1060, and xx 1065. Current activity level may be low, moderate, intense, or some other label, and can be determined by the type of activity, the speed of the activity, and other factors. The levelling wheel determines the level at which the activity is being presented to the user. The level 1020 is the level at which the user is performing the workout. The heart rate is determined based on the spatiotemporal data as described herein. The count of exercises performed 1030 and exercise type graphic can be determined by processing the spatiotemporal data (recognition of the exercise type and count of times performed) and/or retrieved by the application. The Application name 1045 is retrieved by detection of the application at execution. The calories counted 1040 and 1050 is determined by processing the spatiotemporal data as described herein. The total daily calories is determined by accumulation of the workouts done in a particular day, and the experience points (XP) is determined by based on the number of workouts, similar and otherwise, performed by the user historically.

Figure 11:
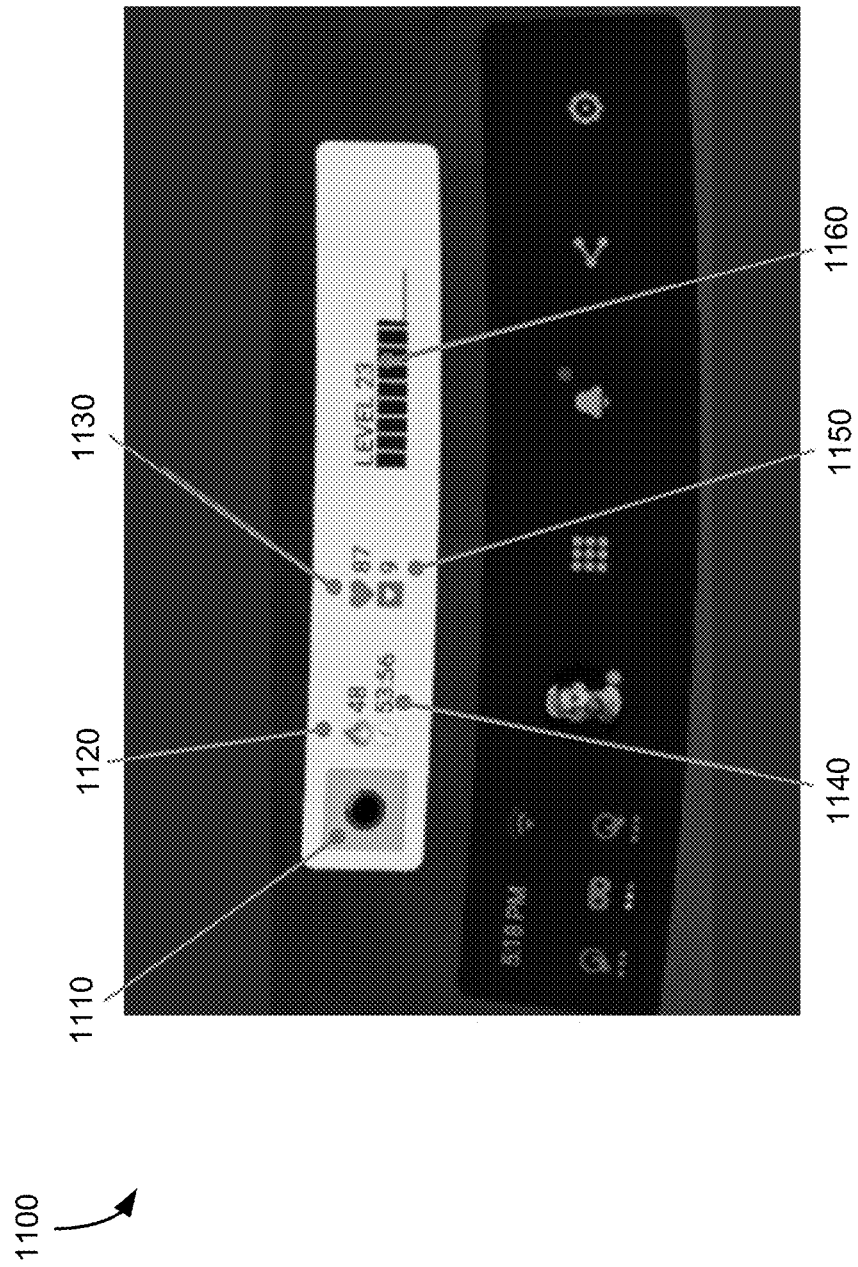
FIG. 11 is an exemplary overlay for use with a virtual reality device or augmented reality device.

FIG. 11 is an exemplary overlay 1100 for use with a virtual reality device or augmented reality device. Overlay 1100 of FIG. 11 displays, during a virtual reality experience or augmented reality experience, calories burned, heart rate data, level and experience information, and other information. The overlay can be displayed within the user's view, such as above the direction currently viewed by the user, off to a side, top or bottom of the user's current view, or some other location within the virtual reality experience or augmented reality space.

Overlay 1100 displays a levelling wheel 1110, calories burned 1120, estimated heart rate 1130, current workout time 1140, number of exercise (e.g., number of squats performed) 1150, and level information 1160. The levelling wheel 1110 identifies the level at which the activity is being presented to the user. The calories burned 1120 is determined by processing the spatiotemporal data as described herein. The heart rate 1130 is determined based on the spatiotemporal data as described herein. The exercise count 1150 can be determined by processing the spatiotemporal data (recognition of the exercise type and count of times performed) and/or retrieved by the application. The level 1160 is the level at which the user is performing the workout.

Figure 12:
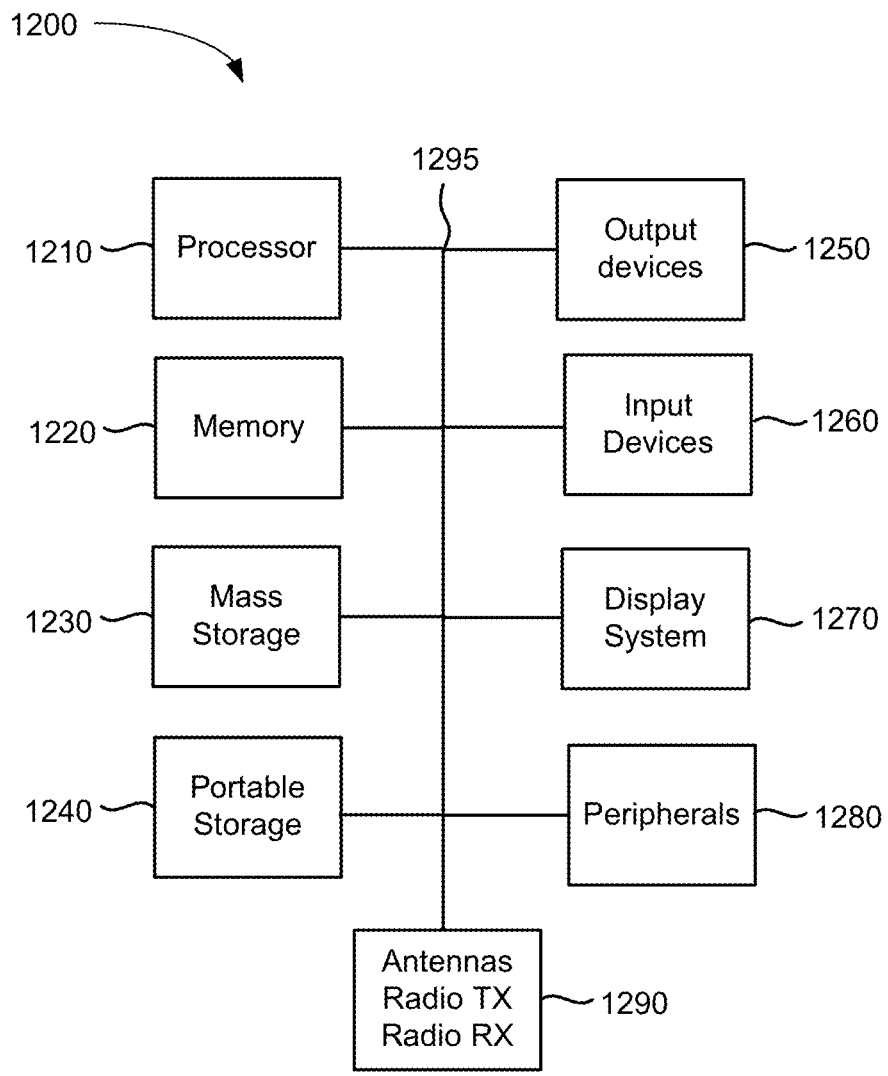
FIG. 12 is a block diagram of a computing environment for implementing the present technology.

FIG. 12 is a block diagram of a computing environment for implementing the present technology. System 1200 of FIG. 12 may be implemented in the contexts of the likes of machines that implement battery client 110 and server 120. The computing system 1200 of FIG. 12 includes one or more processors 1210 and memory 1220. Main memory 1220 stores, in part, instructions and data for execution by processor 1210. Main memory 1220 can store the executable code when in operation. The system 1200 of FIG. 12 further includes a mass storage device 1230, portable storage medium drive(s) 1240, output devices 1250, user input devices 1260, a graphics display 1270, and peripheral devices 1280.

The components shown in FIG. 12 are depicted as being connected via a single bus 1290. However, the components may be connected through one or more data transport means. For example, processor unit 1210 and main memory 1220 may be connected via a local microprocessor bus, and the mass storage device 1230, peripheral device(s) 1280, portable storage device 1240, and display system 1270 may be connected via one or more input/output (I/O) buses.

Mass storage device 1230, which may be implemented with a magnetic disk drive, an optical disk drive, a flash drive, or other device, is a non-volatile storage device for storing data and instructions for use by processor unit 1210. Mass storage device 1230 can store the system software for implementing embodiments of the present invention for purposes of loading that software into main memory 1220.

Portable storage device 1240 operates in conjunction with a portable non-volatile storage medium, such as a floppy disk, compact disk or Digital video disc, USB drive, memory card or stick, or other portable or removable memory, to input and output data and code to and from the computer system 1200 of FIG. 12. The system software for implementing embodiments of the present invention may be stored on such a portable medium and input to the computer system 1200 via the portable storage device 1240.

Input devices 1260 provide a portion of a user interface. Input devices 1260 may include an alpha-numeric keypad, such as a keyboard, for inputting alpha-numeric and other information, a pointing device such as a mouse, a trackball, stylus, cursor direction keys, microphone, touchscreen, accelerometer, and other input devices. Additionally, the system 1200 as shown in FIG. 12 includes output devices 1250. Examples of suitable output devices include speakers, printers, network interfaces, and monitors.

Display system 1270 may include a liquid crystal display (LCD) or other suitable display device. Display system 1270 receives textual and graphical information and processes the information for output to the display device. Display system 1270 may also receive input as a touchscreen.

Peripherals 1280 may include any type of computer support device to add additional functionality to the computer system. For example, peripheral device(s) 1280 may include a modem or a router, printer, and other device.

The system of 1200 may also include, in some implementations, antennas, radio transmitters and radio receivers 1290. The antennas and radios may be implemented in devices such as smartphones, tablets, and other devices that may communicate wirelessly. The one or more antennas may operate at one or more radio frequencies suitable to send and receive data over cellular networks, Wi-Fi networks, commercial device networks such as a Bluetooth device, and other radio frequency networks. The devices may include one or more radio transmitters and receivers for processing signals sent and received using the antennas.

The components contained in the computer system 1200 of FIG. 12 are those typically found in computer systems that may be suitable for use with embodiments of the present invention and are intended to represent a broad category of such computer components that are well known in the art. Thus, the computer system 1200 of FIG. 12 can be a personal computer, handheld computing device, smart phone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Android, as well as languages including Java, .NET, C, C++, Node.JS, and other suitable languages.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. A method for determining energy expense, the method comprising:
   receiving spatiotemporal data by a client application executing on a client device based on tracking position of a plurality of sensors configured to be placed on a user's one or more body parts,
   a plurality of activity elements associated with a workout being displayed on a display responsive to the client application,
   the spatiotemporal data indicating spatial coordinates of a plurality of points associated with the user's one or more body parts as obtained from the tracking of the position of the plurality of sensors in three dimensional space, while the user is performing the workout by moving the user's one or more body parts on which the sensors are placed,
   the spatiotemporal data expressed over time and being sampled periodically, in response to the user moving the one or more body parts during the workout;
   determining the energy expense for the user during the workout based on the spatiotemporal data, captured over a predetermined period of time, and a predetermined resting energy expense, the energy expense being adjustable based on user biometric data and nature of activity the user is engaged in based on input provided to the client application;
   adjusting the energy expense based on the user biometric data and the nature of the activity; and
   displaying the energy expense by the user during the workout on the display with the activity elements within the display.

2. The method of claim 1, wherein the spatiotemporal data is received as data derived from image data of the user performing the workout and the biometric data includes at least the user's body mass index (BMI).

3. The method of claim 1, wherein the energy expense includes calories burned.

4. The method of claim 3, wherein the energy expense and calories burned are displayed as an overlay to the activity elements displayed in a virtual reality (VR) or augmented reality (AR) visual space.

5. The method of claim 1, wherein the activity elements are augmented elements displayed within space captured by a camera.

6. The method of claim 1, wherein the user biometric data comprises the user age, height, weight, and sex.

7. The method of claim 1, wherein determining the energy expense includes:
selecting one of a plurality of calculation methods; and
calculating the energy expense based on the selected calculation method.

8. The method of claim 1, wherein determining the energy expense includes comparing the energy expense to a range of expected energy expenses to confirm validity of the energy expense.

9. The method of claim 1, wherein determining the energy expense comprises:
transmitting the received spatiotemporal data to a remote server by the client device;
and
receiving a calculated energy expense by from the remote server by the client device.

10. The method of claim 1, wherein
an estimated heart rate for the user is determined while performing the workout based on the spatiotemporal data and the user biometric data that does not change during the workout,
the energy expense for the user during the workout is determined based on the spatiotemporal data and the estimated user heart rate, the user heart rate and the energy expense being determined without measuring the user's heart rate, and
the estimated heart rate for the user is displayed during the workout by the client application.

11. A non-transitory computer readable storage medium having embodied thereon a program, the program being executable by a processor to perform operations comprising:
receiving spatiotemporal data by a client application stored and executing on a client device, a plurality of activity elements associated with a workout being displayed on a display in communication with the client application, the spatiotemporal data indicating spatial coordinates of a plurality of points associated with a plurality of a user's body parts, while the user is performing the workout, the spatiotemporal data being updated periodically, in response to the user moving one or more body parts, from among the plurality of the user's body parts, during the workout;
determining an energy expense for the user during the workout based on the spatiotemporal data, captured over a predetermined period of time, and a predetermined resting energy expense, the energy expense being adjustable based on user biometric data and nature of activity the user is engaged in based on input provided to the client application;
adjusting the energy expense based on the user biometric data and the nature of the activity; and
displaying the energy expense by the user during the workout on the display with the activity elements within the display.

12. The non-transitory computer readable storage medium of claim 11, wherein the spatiotemporal data is received as data derived from image data of the user performing the workout.

13. The non-transitory computer readable storage medium of claim 11, wherein the energy expense includes calories burned.

14. The non-transitory computer readable storage medium of claim 11, wherein the energy expense and the calories burned are displayed as an overlay to the activity elements, wherein the activity elements are augmented elements displayed within space captured by a camera.

15. A system comprising:
a server including memory and one or more processors performing operations to:
receive spatiotemporal data from a client application stored and executing on a client device,
the client application rendering activity elements associated with a user workout in a virtual reality (VR) visual space or an augmented reality (AR) visual space, and
the spatiotemporal data indicating the spatial coordinates of a plurality of points associated with a user's body while the user is performing the workout;
determine an estimated heart rate for the user while performing the workout based on the spatiotemporal data and user biometric data;
determine an energy expense for the user during the workout based on the spatiotemporal data and the estimated user heart rate; and
forward the energy expense by the user and the estimated heart rate for the user during the workout to the client device for display by the client application, the client application rendering energy expense information with the activity elements within the virtual reality (VR) visual space or the augmented reality (AR) visual space.

16. The system of claim 15, wherein the spatiotemporal data is data derived from image data of the user performing the workout and the biometric data includes at least the user's body mass index (BMI).

17. The system of claim 15, wherein the energy expense includes calories burned.

18. The system of claim 16, wherein the energy expense and calories burned are displayed as an overlay to the activity elements displayed in the virtual reality (VR) visual Space or the augmented reality (AR) visual space.

19. The system of claim 15, wherein the activity elements are augmented elements displayed within space captured by a camera.

20. The system of claim 15, wherein the user biometric data comprises the user age, height, weight, and sex.

21. The system of claim 15, wherein determining the energy expense comprises:
selecting one of a plurality of calculation methods; and
calculating the energy expense based on the selected calculation method.

22. The system of claim 15, wherein determining the energy expense includes comparing the energy expense to a range of expected energy expenses to confirm validity of the energy expense.

23. The system of claim 15, wherein determining the energy expense comprises:
transmitting the received spatiotemporal data to a remote server by the client device;
and
receiving a calculated energy expense from the remote server by the client device.

24. The system of claim 15, wherein: the estimated heart rate for the user is determined while performing the workout based on the spatiotemporal data and the user biometric data that does not change during the workout, the energy expense for the user during the workout is determined based on the spatiotemporal data and the estimated user heart rate, the user heart rate and the energy expense being determined without measuring the user's heart rate, and the estimated heart rate for the user is displayed during the workout by the client application.

\* \* \* \* \*